(12) United States Patent
Gao

(10) Patent No.: US 9,090,660 B2
(45) Date of Patent: Jul. 28, 2015

(54) PEPTIDE-BOUND GOLD METAL NANO-CLUSTERS AS CANCER CELL KILLING AGENTS

(71) Applicant: Xueyun Gao, Beijing (CN)

(72) Inventor: Xueyun Gao, Beijing (CN)

( * ) Notice: Subject to any disclaimer, the term of this patent is extended or adjusted under 35 U.S.C. 154(b) by 47 days.

(21) Appl. No.: 13/787,936

(22) Filed: Mar. 7, 2013

(65) Prior Publication Data

US 2014/0256038 A1    Sep. 11, 2014

(51) Int. Cl.
*C07K 7/08* (2006.01)
*C07K 7/06* (2006.01)

(52) U.S. Cl.
CPC .... *C07K 7/08* (2013.01); *C07K 7/06* (2013.01)

(58) Field of Classification Search
None
See application file for complete search history.

(56) References Cited

U.S. PATENT DOCUMENTS

| 8,383,919 B2 * | 2/2013 | Gao | 530/300 |
| 2008/0241258 A1 * | 10/2008 | Brandau et al. | 424/489 |
| 2011/0118441 A1 * | 5/2011 | Gao | 530/345 |

OTHER PUBLICATIONS

Koster et al. Chem. Sci. 3;2062-2072:2012.*
Koster et al. Chem Sci. 2012.*

* cited by examiner

*Primary Examiner* — Amber D Steele
*Assistant Examiner* — Schuyler Milton
(74) *Attorney, Agent, or Firm* — Jie Tan; JT Law Office

(57) ABSTRACT

Peptide-bound gold metal nanocluster complexes are produced to induce cancer cell death by dramatically inhibiting TrxR activities of the cancer cells. Specificity is shown by selectively designing peptide sequences.

17 Claims, 7 Drawing Sheets

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1

Cys Cys Tyr Arg Phe Lys
1               5

<210> SEQ ID NO 2
<211> LENGTH: 13
<212> TYPE: PRT
<213> ORGANISM: Artificial Sequence
<220> FEATURE:
```

```
<223> OTHER INFORMATION: Synthetic peptide

<400> SEQUENCE: 2

Cys Cys Tyr Gly Gly Pro Lys Lys Lys Arg Lys Val Gly
1               5                   10

<210> SEQ ID NO 3
<211> LENGTH: 6
<212> TYPE: PRT
<213> ORGANISM: Artificial sequence
<220> FEATURE:
<223> OTHER INFORMATION: Synthetic peptide

<400> SEQUENCE: 3

Lys Cys Cys Tyr Ser Leu
1               5
```

PEPTIDE-BOUND GOLD METAL NANO-CLUSTERS AS CANCER CELL KILLING AGENTS

DESCRIPTION OF RELATED ART

The present application relates to a method and system for killing cancer cells, and more particularly to, peptide gold metal nano-clusters as agents for killing cancer cells.

Note that the points discussed below may reflect the hindsight gained from the disclosed inventions, and are not necessarily admitted to be prior art.

Battles against cancers have been fought among all human populations. Yet cancers remain one of the most fatal diseases. New methods for detections and treatments have greatly improved cancer care in the US. One of the constant themes in the modern medical research is to find new methods and new agents for killing cancers.

Thioredoxin (Trx), together with thioredoxin reductase (TrxR) and NADPH comprising the thioredoxin system, is a hydrogen donor for enzymatic synthesis of cytidine deoxyribonucleoside diphosphate by ribonucleotide reductase. Years of studies of the mechanism and kinetics of the Trx system show that the Trx system is the cells' major protein disulfide reduction system, perhaps is the physiological equivalent of a reducing agent like dithiothreitol.

Since ribonucleotide reductase catalyzes the rate limiting step in deoxyribonucleotide synthesis, ribonucleotide reductase is essential for DNA replication and repair. Also a large number of transcription factors are regulated via redox signaling by Trx, TrxR and Ref-1, many are related with cell growth. Due to the high growth nature of cancer cells, most cancer cells have a high level of expression of Trx and TrxR, which has been assumed to be a protection against apoptosis and promote cell growth. TrxR is an important target for cancer therapy and drug development. Trx system therefore is one of the most important target enzymes for drug development.

Gold compounds have long been shown to possess potent antitumor activity against some cancer cells by inhibiting TrxR activities. However, the effects of these gold compounds are limited by their poor cellular uptake as some of them do not readily enter cells. Additionally, for example, auranofin's high reactivity with protein thiols also limits their antitumor activity in vivo. The development of Au(I) complexes with chelated diphosphines such as [Au(dppe)$_2$]Cl with its aim of reducing the high thiol reactivity of auranofin and analogs shows a severe toxicity, a consequence of the non-selective concentration of compounds into mitochondria of both tumourigenic and non-tumourigenic cells, causing general membrane permeabilisation.

It remains a difficult task to selectively kill tumor cells. Nanotechnology, the use of materials of sizes ranging from 1 to 100 nm, has shown great promises and offers a new angle in drug designs in providing diagnostic and therapeutic agents for treating cancers. More than 20 FDA-approved diagnostic or therapeutic nanotechnologies are in clinical use and several hundred more in clinical development.

Gold-nanoparticles conjugated with tumor cell specific ligands have been shown to selectively accumulate to tumor cells. They are then used to facilitate highly efficient photothermal ablation by exposing to non-invasive near-infrared lasers. Conjugated gold-nanoparticles, decorated with both the cell-penetrating RGD peptide and a nuclear localization sequence peptide, have also been observed to cause tumor cell apoptosis by the mechanism of preferential single strand DNA binding, oxidative stress and the production of free oxygen radicals.

However, conjugated gold-nanoparticles (generally larger than 10 nm) sometimes are too large to enter into inner cells, and the processes of producing suitably conjugated gold-nanoparticles are tedious and not easy to control. The manipulation of near-infrared (NIR) laser exposure may not be sufficiently cost effective and the final results of such treatment require the perfection of the NIR technology itself. The results of accumulations of cyclic RGD-targeted gold nanoparticles in tumors are also not consistent.

Gold metal nanoclusters have proved to be an advantageous alternative to gold nano-particles in that they can be made very small in size (<10 nm) and are stable and nontoxicity to cells. Gold metal nanoclusters have been immobilized with specific biomolecule to study functionality of organelle or intracellular biomolecular targets. For example, gold metal nanoclusters synthesized with mercaptoundecanoic acid (MUA) can be further modified with the nuclear localization signal peptide via 1-Ethyl-3-(3-dimethylaminopropyl) carbodiimide activation to mark nucleolus. See Lin, S. Y., et al., *Chemical Communication*, 39, pp 4762-4764 (2008).

In the U.S. Pat. No. 8,383,919, the content of which is incorporated by reference herein, the inventor of this application developed a simple, one step method for producing highly fluorescent and peptide-bound gold metal nano-cluster complexes that readily enter into cellular compartments. Those peptide-bound gold metal nano-clusters have shown great potential for sub-cellular biolabeling and bioimaging, and for potential cancer diagnostics.

In this invention, the inventor surprisingly discovers that the peptide-bound gold metal nanoclusters as prepared in U.S. Pat. No. 8,383,919, much smaller in sizes than gold-nanoparticles, not only can readily enter into sub-cellular compartments but also are capable of causing apoptotic cell death of cancer cells by inhibiting TrxR activities.

This new discovery presents a new and great potential for the peptide-bound gold metal nanoclusters to be used as therapeutic agents. The difference in apoptotic induction mechanism to that of peptide conjugated gold nano-particles may suggest potentially wider pharmacokinetic applications. The peptide-bound gold metal nanoclusters therefore show great potential as the alternative to gold compound agents to be developed for specifically targeting cancer cells with improved cellular uptake and cell toxicity. Furthermore, peptide-bound gold nanoparticles can also serve as a designing tool and system for cancer drug screenings and delivery studies.

SUMMARY

The present application discloses a new system and method for inhibiting cancer cell growth and causing cell death to cancer cells.

In one embodiment, peptide-bound gold metal nanoclusters are produced by a one-step reaction of mixing a gold salt solution with a cell targeting specific peptide containing an N-terminal or C-terminal amino acid selected from Arg, Asn, Asp, Cys, Gln, Glu, His, Trp, and/or Tyr. Cancer cells are then caused to become apoptotic by exposing to said peptide-bound gold metal nanoclusters over a period of time which dramatically inhibit TrxR activities.

In one embodiment, the peptide contains a nuclear localization signal sequence.

In another embodiment, the peptide contains a mitochondria sequence motif for targeting to mitochondria.

In another embodiment, the peptide contains a binding motif for a tyrosine kinase.

The disclosed innovation, in various embodiments, provide one or more of at least the following advantages. However, not all of these advantages result from every one of the innovations disclosed, and this list of advantages does not limit the various claimed inventions.

The inhibition of TrxR activities by peptide-bound gold metal nanocluster complexes shows great potential for the peptide-bound gold metal nanoclusters to be used as cancer therapeutic agents. As an alternative to gold compounds, peptide-bound gold metal nanoclusters have great advantages and potentials to be developed for targeting specific cancer cells with improved cellular uptake and cell toxicity. Further more, peptide-bound gold nanoparticle complexes can also be developed to serve as designing tools and systems for cancer drug screenings and delivery studies.

BRIEF DESCRIPTION OF THE DRAWINGS

The disclosed application will be described with reference to the accompanying drawings, which show important sample embodiments of the invention and which are incorporated in the specification hereof by reference, wherein:

FIG. 1A is about the Pep V-Au nano-clusters; FIG. 1B is about Pep H-Au nano-clusters; FIG. 1C is about Pep M-Au nano-clusters, in accordance with this application.

FIG. 2A shows the image of Hela cells incubated with Pep V-Au nano-clusters; FIG. 2B shows the image of HT-29 cells incubated with Pep H-Au nano-clusters; FIG. 2C shows the image of A549 cells incubated with Pep M-Au nano-clusters, in accordance with this application.

FIG. 3A shows the cell viability of Hela cells with Pep V-Au nano-clusters; FIG. 3B shows the cell viability of HT-29 cells with Pep H-Au nano-clusters; FIG. 3C shows the cell viability of A549 cells with Pep M-Au nano-clusters, in accordance with this application.

FIG. 4A shows the TrxR enzyme activities of Hela cells with Pep V-Au nano-clusters; FIG. 4B shows the TrxR enzyme activities of HT-29 cells with Pep H-Au nano-clusters; FIG. 4C shows the TrxR enzyme activities of A549 cells with Pep M-Au nano-clusters, in accordance with this application.

DETAILED DESCRIPTION OF SAMPLE EMBODIMENTS

Figures 1A, 1B, 1C:
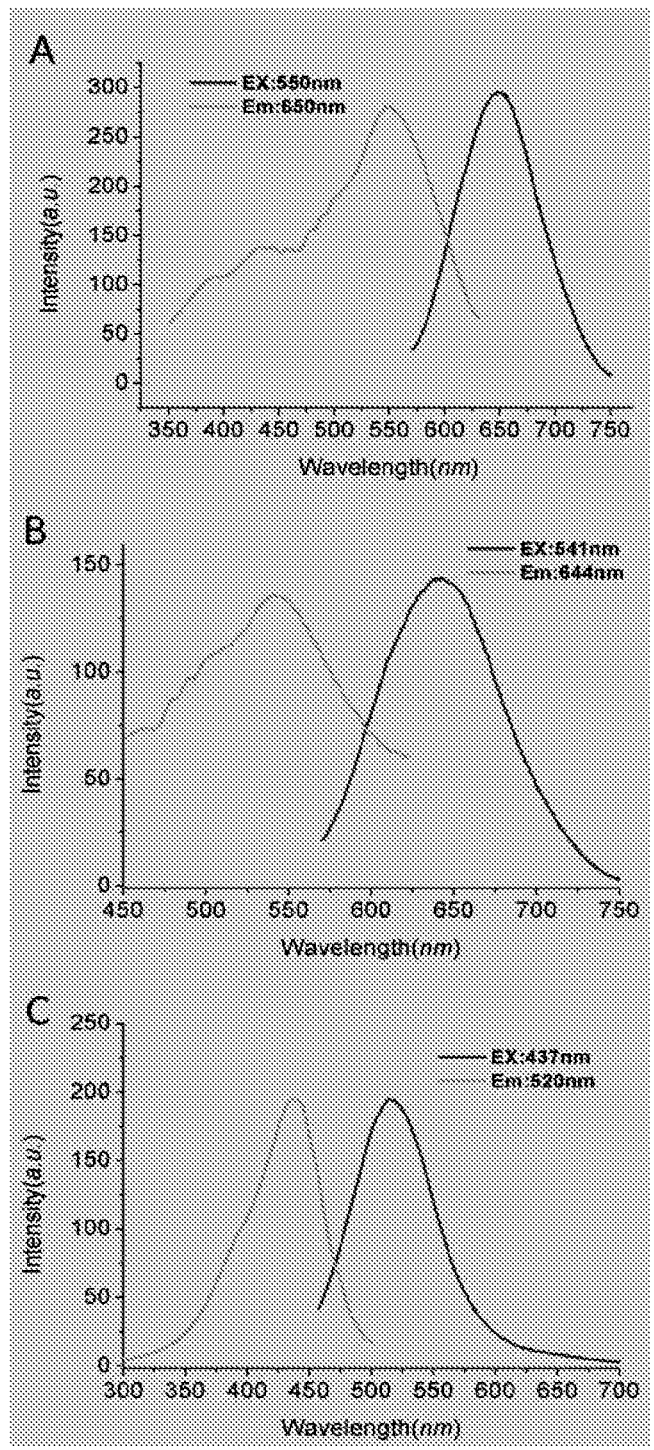
FIGS. 1A, 1B, and 1C show the excitation and emission spectrums of the three peptide-gold metal nano-clusters.

The numerous innovative teachings of the present application will be described with particular reference to presently preferred embodiments (by way of example, and not of limitation). The present application describes several embodiments, and none of the statements below should be taken as limiting the claims generally.

For simplicity and clarity of illustration, the drawing figures illustrate the general manner of construction, and description and details of well-known features and techniques may be omitted to avoid unnecessarily obscuring the invention. Additionally, elements in the drawing figures are not necessarily drawn to scale, some areas or elements may be expanded to help improve understanding of embodiments of the invention.

The terms "first," "second," "third," "fourth," and the like in the description and the claims, if any, may be used for distinguishing between similar elements and not necessarily for describing a particular sequential or chronological order. It is to be understood that the terms so used are interchangeable. Furthermore, the terms "comprise," "include," "have," and any variations thereof, are intended to cover non-exclusive inclusions, such that a process, method, article, apparatus, or composition that comprises a list of elements is not necessarily limited to those elements, but may include other elements not expressly listed or inherent to such process, method, article, apparatus, or composition.

It is contemplated and intended that any peptides with functions to target an intracellular compartments may be designed and synthesized to contain an amino acid of Arg, Asn, Asp, Cys, Gln, Glu, His, Trp, and/or Tyr at the N-terminal or C-terminal of the peptide. Chimerical peptide sequences having various functionalities may be designed and synthesized, for example, ligand peptide sequences binding to different receptor domains may be combined with crossing membrane domains or signal peptide for cellular trafficking. However, the current application is not limited to peptides with a particular primary sequences. Any peptides that targets to cellular compartments may be used for generating peptide-gold metal complex, and for the application of this invention.

For clarity reasons, the examples in this application are conducted with three known and published peptide sequences with the addition of a Cys amino acid at the N-terminal if the sequence itself does not provide one. The peptide Pep-M has a primary amino acid sequence of Cys-Cys-Tyr-D-Arg-Phe-Lys (SEQ ID NO: 1), where the Cys-Tyr-D-Arg-Phe-Lys is a known cell permeable, mitochondrial-targeted peptide antioxidant. See Hazel H. Szeto, Chapter 31, "Cell-Permeable, Mitochondrial-Targeted, Peptide Antioxidants" in *Drug Addiction*, edited by R. S. Rapaka and W. Sadee, published by American Association of Pharmaceutical Scientists, 2008. This peptide not only targets to mitochondria, but also functions as an antioxidant that potently inhibits oxidative stress caused cell death. Because this peptide actually prevents cell death caused from oxidative stress, the cancer killing effect of Pep M-Au nano-cluster complexes observed in this application should largely be due to the inhibition of TrxR enzyme activities.

The peptide Pep V has a primary amino sequence of Cys-Cys-Tyr-Gly-Gly-Pro-Lys-Lys-Lys-Arg-Lys-Val-Gly (SEQ ID NO: 2) where Cys-Tyr-Gly-Gly-Pro-Lys-Lys-Lys-Arg-Lys-Val-Gly is a well known Nuclear Localization Signal (NLS) peptide from SV40 large T. When this peptide was added to Hela cell cultures, it was shown to be able to escape the endosomal pathway and reach the nuclear membrane, and to be clustered around the cytoplasmic side of the nuclear membrane of Hela cells. See A. G. Tkachenko, et al. "Cellular Trajectories of Peptide-Modified Gold Particle Complexes: Comparison of Nuclear Localization Signals and Peptide Transduction Domains," *Bioconjugate Chem.* 2004, 15, pp 482-490.

The peptide Pep H has a primary sequence of Lys-Cys-Cys-Tyr-Ser-Leu (SEQ ID NO: 3). This peptide is a well known binding ligand for tyrosin kinase ErbB-2 that is overexpressed in the cytoplasm of breast, prostate, lung, gastric and ovarian carcinomas. See S. L Deutscher, et al. "[111]In-labeled KCCYSL peptide as an imaging probe for ErbB-2 expressing ovarian carcinomas," *J Labelled Coumpounds and Radiopharmaceuticals,* 2009, 52, 583-590.

1.1. Synthesis of Peptide-Au Nano-Cluster Complexes

All chemicals were purchased from Sigma-Aldrich, unless otherwise indicated. Ultrapure Millipore (Mini-Q) water (18.2 MΩ) was used throughout the experiments. The peptides Cys-Cys-Tyr-D-Arg-Phe-Lys (Pep M), and Cys-Cys-Tyr-Gly-Gly-Pro-Lys-Lys-Lys-Arg-Lys-Val-Gly (Pep V) and Lys-Cys-Cys-Tyr-Ser-Leu (Pep H) were chemically synthesized by a solid phase method by GL Biochem (shanghai) Ltd, Purity: 95%. All glassware were washed with aqua regia (concentrated HCl:concentrated $HNO_3$, volume ratio=3:1), and then rinsed with ultrapure water and ethanol.

In a typical preparation, an aqueous solution of $HAuCl_4$ (25 mM, 16 μL) was slowly added to a solution of peptide (1.06 mM, 376 μL) in a 5 mL vial under vigorous stirring. NaOH (0.5 M, 8 μL) was added within 30 seconds to give a final pH of ~12. The mixture was then sealed and stored in the dark for 12 hours without any disturbance to produce the peptide-Au nano-cluster complexes. After the reaction, the sample was concentrated by a dialysis tube (Merck, Midi D-tube, MWCO: 3000, 50-800 μL) to remove un-reacted free peptides, free NaOH, and free $HAuCl_4$. The obtained peptide-Au nano-cluster complexes are suspended in the water and kept in dark at 4~10° C.

The thus obtained peptide-Au nano-cluster complex sample products are stable either at room temperature or 4-10° C. for at least three months. The products are tested with the excitation and emission spectrums. FIGS. 1A, 1B and 1C show their unique excitation and emission spectrums of the Pep V, Pep M, and Pep H peptide-Au nano-cluster complexes, where FIG. 1A shows the excitation and emission spectrum of Pep V-Au nano-cluster complexes with excitation peak at 550 nm and emission peak at 650 nm; FIG. 1B shows the excitation and emission spectrum of Pep H-Au nano-cluster complexes with excitation peak at 541 nm and emission peak at 644 nm; FIG. 1C shows the excitation and emission spectrum with excitation peak at 437 nm and emission peak at 520 nm of Pep M-Au nano-cluster complexes. All samples show sharp peaks of the excitation and emission spectrums at different wavelengths, i.e. with different fluorescent colors.

1.2. Cell Culture

Human lung cancer A549, human cervical cancer cell lines Hela and human colorectal adenocarcinoma cell HT-29 were purchased from the American Type Culture Collection (Manassas, Va., USA). A549 and Hela cells were cultivated in DMEM-HEPES-high glucose medium cell culture purchased from Thermo Scientific, Inc, and supplemented with 10% fetal bovine serum purchased from Gibco, Life Technologies, Inc, and 1% penicillin streptomycin solution (from Thermo Scientific, Inc) in a humidified incubator with 5% $CO_2$ at 37° C. HT-29 was similarly cultivated in DMEM/F12 (1:1) medium from Thermo Scientific, Inc.

1.3. Confocal Laser Scanning Microscopic Observation

Cellular uptake and intracellular distribution of peptide-Au nano-cluster complexes were observed by using Confocal Laser Scanning Microscope (CLSM, UltraVIEW Vox+Nikon from PerkinElmer, Inc). Various cell lines were planted on a 35 mm glass-based dish at about $5 \times 10^5$ cells/well for 24 hours. Then cells are incubated with fresh culture medium containing of one type of peptide-Au nano-cluster complexes at a concentration of 0.5 mM Au for 5 hours. Hela cells were incubated with Pep V-Au nano-clusters, HT-29 cells were incubated with Pep H-Au nano-clusters, and A549 cells were incubated with Pep M-Au nano-clusters. The incubated cells were then washed with saline water and observed under the Confocal Laser Scanning Microscope with the excitation wavelength at 561 nm, 561 nm, or 450 nm for Pep V-Au nano-clusters, Pep H-Au nano-clusters or Pep M-Au nano-clusters respectively.

Figure 2A:
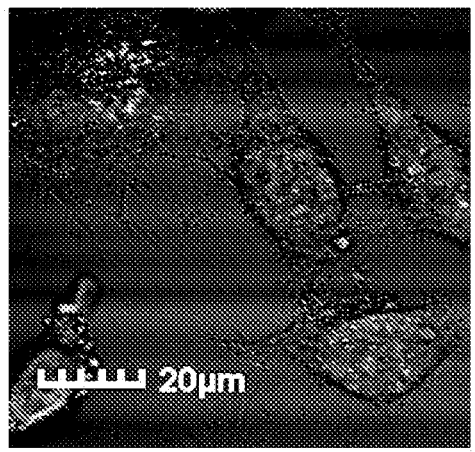
FIGS. 2A, 2B and 2C show the Confocal Laser Scanning Microscopic images of various cancer cells treated with various peptide-gold metal nano-clusters for 5 hrs.
Figure 2B:
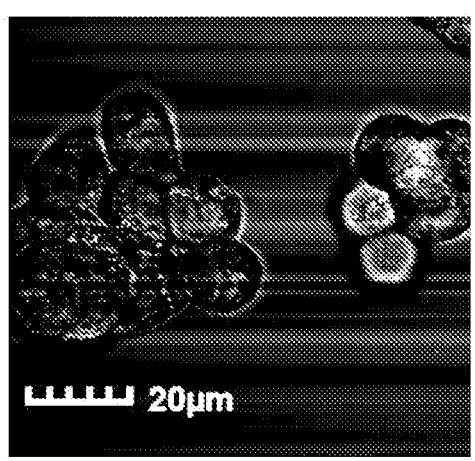
Figure 2C:
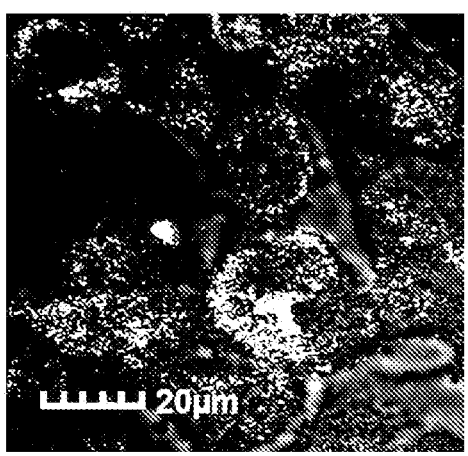

In reference to FIGS. 2A, 2B and 2C, the fluorescent cell images are shown, where the bright dots are generated from the fluorescent light emissions of the various peptide-Au nano-clusters. FIG. 2A shows that Pep V-Au nano-clusters entered into the cytoplasm of Hela cells, some were located inside the nucleus some were located outside but near the nucleus. FIG. 2B shows that Pep H-Au nano-clusters entered into the cytoplasm of HT-29 cells. FIG. 2C shows that Pep M-Au nano-clusters entered into the mitochondria of A549 cells and some enter into cytoplasm of A549.

1.4. Anti-Proliferative Effects

The antiproliferative effects of various peptide-Au nano-cluster complexes were measured by Cell Counting Kit-8 system (CCK-8) according to manufacturer's instructions by Dojindo Laboratory, Inc. Various cell line cells were seeded in 96-well plates at about $1 \times 10^4$ cells/well. After growing overnight, Hela cells were incubated with Pep V-Au nano-cluster complexes, HT-29 cells were incubated with Pep H-Au nano-cluster complexes, and A549 cells were incubated with Pep M-Au nano-cluster complexes having various Au concentrations for 36 hours. Treated cells of each well were collected and 10 ml of CCK-8 solution was added to each of the samples and incubated for 1 hour at 37° C. The absorbance of each of the samples was measured by using a SpectraMax M2 microplate reader with a filter of 450 nm. All data were presented as mean percentages±SEM in triplicate compared to the OD values of none treated cells.

Figure 3A:
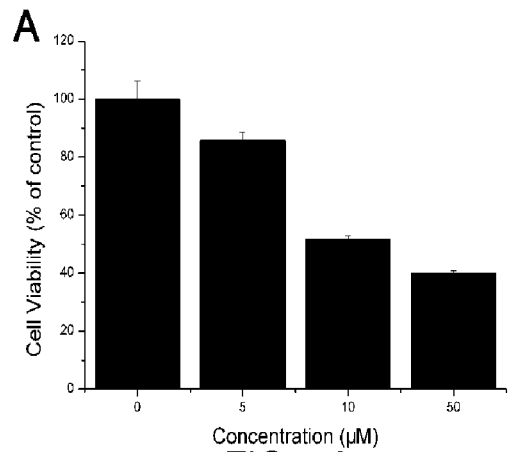
FIGS. 3A, 3B and 3C graphically show the cell viabilities of various cancer cells treated with various peptide-gold metal nano-clusters for 36 hrs.
Figure 3B:
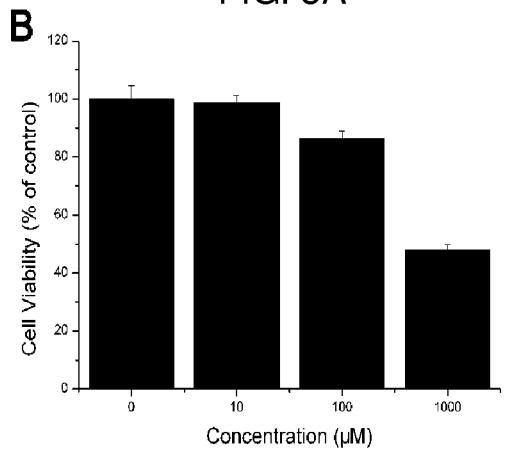
Figure 3C:
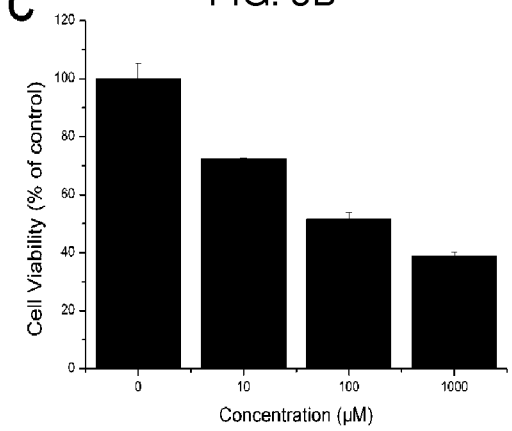

In reference to FIGS. 3A, 3B and 3C, the cell viabilities of the three different cancer cell lines treated with various peptide-gold metal nano-clusters for 36 hrs are shown. FIG. 3A shows the cell viability of Hela cell with Pep V-Au nano-clusters is reduced to 50% at Pep V-Au nano-cluster concentration containing 10 μM Au. FIG. 3B shows the cell viability of HT-29 cell with Pep H-Au nano-clusters is reduced to 40% at Pep H-Au nano-cluster concentration containing 1000 μM Au, however the effect is more limited with lower concentrations of Pep H-Au nano-clusters. FIG. 3C shows the cell viability of A549 cell with Pep M-Au nano-clusters is reduced to 50% at Pep M-Au nano-clusters concentration having 100 μM Au.

Thus different cell lines appear to show different sensitivity to the different peptide-Au nano-clusters. Pep M peptide has been shown to not only target to mitochondria, but also function as an antioxidant that potently inhibits oxidative stress caused cell death. Because this peptide actually prevents cell death caused from oxidative stress, the cancer killing effect of Pep M-Au nano-cluster complexes observed in this application should largely be due to the inhibition of TrxR enzyme activities.

1.5. Thioredoxin Reductase Assay

Hela cells, HT-29 cells and A549 cells were respectively seeded in a 6-well plate and grown to 80% confluence prior to be treated with peptide-Au nano-cluster complexes. After incubating with the different peptide-Au nano-clusters at several different concentrations for 36 hours, cells were harvested, and washed with saline buffer (PBS) and precipitated. The packed cell volumes were extracted with 1 volume of CelLytic M solution from Sigma, Inc. The thioredoxin reductase activities in the cell lysises of various samples were then measured by Thioredoxin Reductase Assay Kit (from Sigma, Inc) according to manufacturer's instructions.

Figure 4A:
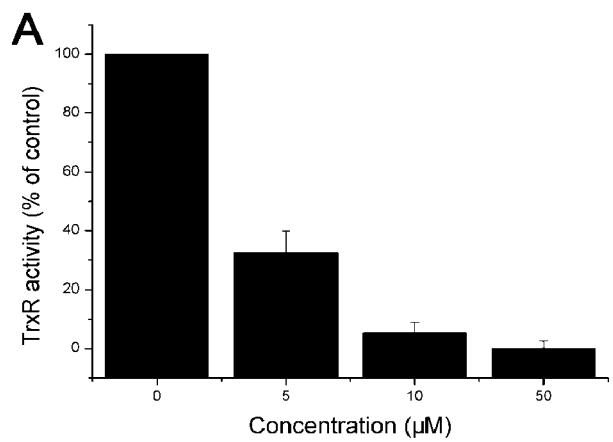
FIGS. 4A, 4B and 4C graphically show the TrxR enzyme activities of various cancer cells treated with various peptide-gold metal nano-clusters for 36 hrs.
Figure 4B:
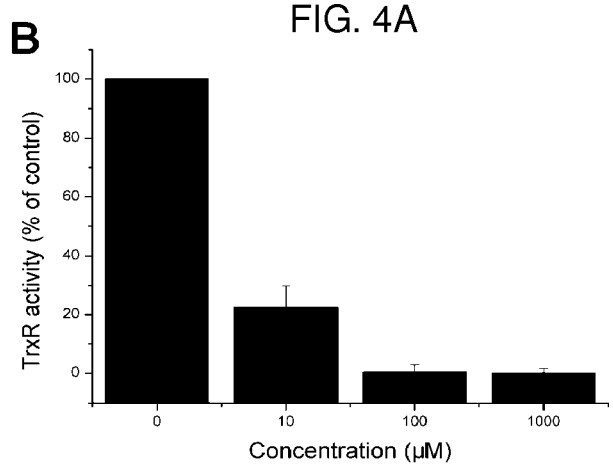
Figure 4C:
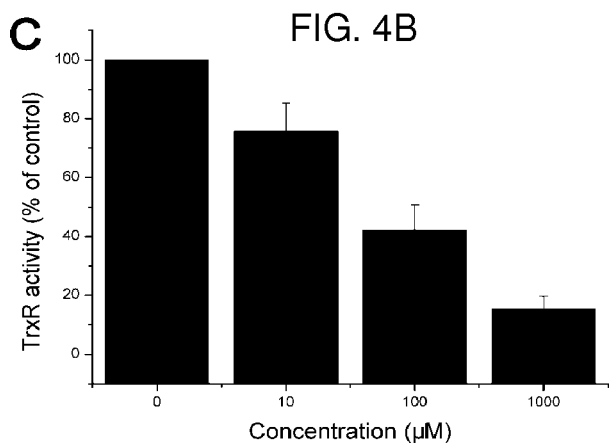

In reference to FIGS. 4A, 4B and 4C, the TrxR enzyme activities of various cancer cells treated with various peptide-gold metal nano-clusters for 36 hours are shown. FIG. 4A shows the TrxR enzyme activities of Hela cell with Pep V-Au nano-clusters, the TrxR enzyme activities were severely inhibited to a background level at Pep V-Au nano-cluster concentration containing 50 μM Au. FIG. 4B similarly shows the TrxR enzyme activities of HT-29 cell with Pep H-Au nano-clusters were severely inhibited to a background level at Pep H-Au nano-cluster concentration containing 100 μM Au. FIG. 4C shows the TrxR enzyme activities of A549 cell with Pep M-Au nano-clusters were also significantly inhibited to 40% at Pep M-Au nano-cluster concentration having 100 μM Au.

The results of FIGS. 3A, 3B and 3C together with FIGS. 4A, 4B and 4C provide a good correlation between the amount of the peptide-Au nano-cluster concentrations and the cell viabilities. Three peptide Au nano-clusters target three different cell lines. The data also demonstrate a good correlation between the severity of inhibition of the TrxR enzyme activities and the cell viabilities.

Thioredoxin reductase (TrxR) is a selenoenzyme belonging to a family of glutathione reductase-like hom-dimeric flavoenzymes. Various observations have demonstrated that cancer cell often overexpress TrxR. Tumor cells appear to be more dependent on TrxR activities, perhaps for the reason of constant requirement of DNA synthesis. Other studies have shown that TrxR has a crucial role in tumor onset and progressions, and have has been suggested as a new target for anticancer drug development.

Figure 5:
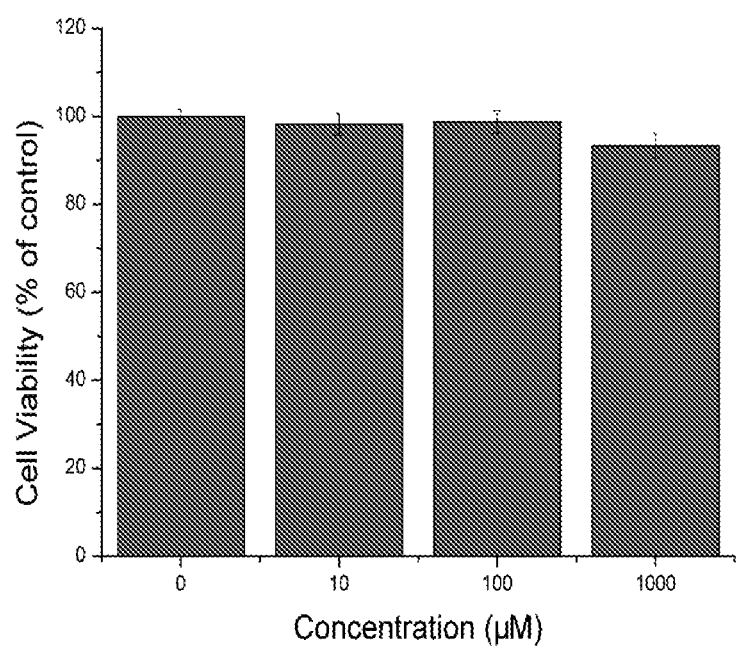
FIG. 5 graphically shows the cell viabilities of H1299 cells treated for 36 hrs with different concentrations of Pep V-Au nano-clusters (µM of gold) in accordance with this application.

However, not all cancer cells are sensitive to peptide-Au nano-cluster treatment. Having shown to induce the Hela cells, human cervical cancer cells, to apoptosis and death at a very low level of concentration, Pep V-Au nano-clusters did not affect the cell viability of H1299 cells, human lung cancer cell line at a Pep V-Au nano-cluster concentration containing even 1000 μM (as shown in FIG. 5).

Figure 6:
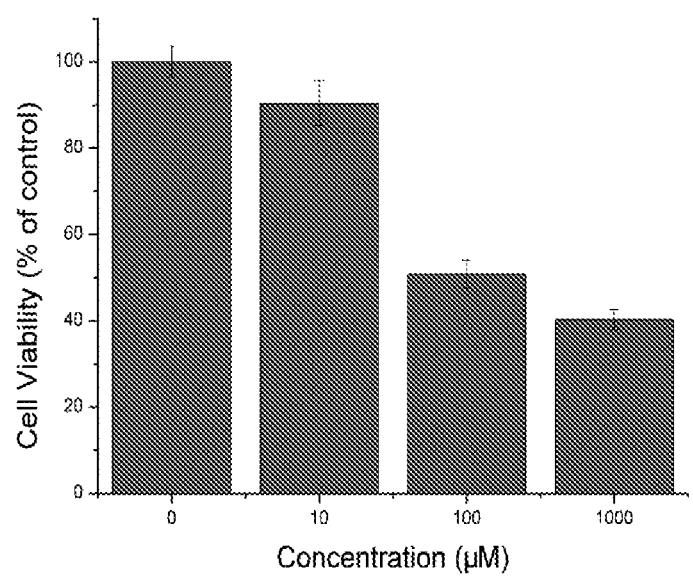
FIG. 6 graphically shows the cell viabilities of MRC-5 cells treated for 36 hrs with different concentrations of Pep V-Au nano-clusters (µM of gold) in accordance with this application.

On the other hand, the MRC-5 cells, a human embryonic lung fibroblast cell line, which does have modest growth rate, show a modest sensitivity to Pep V-Au nano-clusters. At about Pep V-Au nano-cluster concentration containing about 100 μM, the MRC-5 cell viability was reduced to be around 50% (as shown in FIG. 6).

The different sensitivities of the various cell lines towards Pep V-Au nano-clusters appear to be related to the ability of inhibiting the TrxR enzyme activities in these cells by Pep V-Au nano-clusters.

Figure 7:
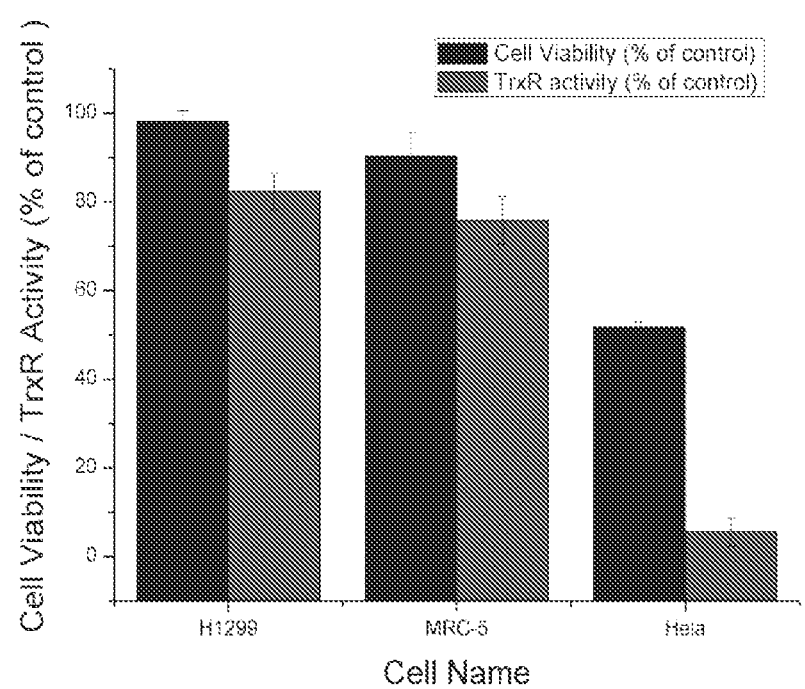
FIG. 7 graphically shows the correlation between the inhibition of TrxR activities and cell viabilities for H1299, MRC-5, and Hela cells treated with Pep V-Au nano-clusters at concentration containing 10 µM of Au for 36 hrs in accordance with this application.

In reference to FIG. 7, a side by side comparison is provided between the various cell lines with the treatment of Pep V-Au nano-clusters. With the treatment of Pep V-Au nano-clusters at concentration containing 10 μM of Au, Hela cells' cell viability was 51.67±1.24%, while that of H1299 cells was 98.21±3.39% and that of MRC-5 cells was 90.32±5.26%. At the same time, the TrxR activities of Hela cells were reduced to 5.36±3.39%, while the TrxR activities of H1299 cells were largely unaffected (82.36±4.12%) and the TrxR activities of MRC-5 cells were modestly affected (75.84±5.32%). These good correlations between cell viabilities in the different cells with the degree of inhibition of TrxR enzyme activities demonstrate that peptide Au nanoclusters can generally induce cell death by inhibition of TrxR enzyme activities.

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

---

What is claimed is:

1. A method of inducing cancer cell death, comprising the steps of:
    preparing a peptide and Au(0) gold metal nano-cluster complex through a preparation of mixing an in-organic gold source with a peptide solution wherein said peptide contains a primary amino acid sequence targeting a type of cancer cells; and
    exposing said cancer cells to said peptide and Au(0) gold metal nano-cluster complex molecules; and
    causing said cancer cell death at a concentration of said peptide and Au(0) gold metal nano-cluster complex molecules that inhibit TrxR enzyme activities of said cancer cells.

2. The method of claim 1, wherein said peptide has an N-terminal and/or C-terminal having an amino acid of either Arg, Asn, Asp, Cys, Gln, Glu, His, Trp, or Tyr.

3. The method of claim 1, wherein said peptide contains nuclear localization signal sequence.

4. The method of claim 1, wherein said peptide contains a primary sequence targeting to a tyrosine kinase.

5. The method of claim 1, wherein said peptide contains a mitochondria targeting primary sequence.

6. The method of claim 1, wherein said concentration of said peptide and Au(0) gold metal nano-cluster complex molecules contains less than 100 μM gold.

7. A method of inducing cancer cell death, comprising the steps of:
    exposing said cancer cells to a concentration of peptide and Au(0) gold metal nano-cluster complex molecules that inhibit TrxR enzyme activities of said cancer cells, wherein said peptide and gold metal nano-cluster complex molecules are prepared through a preparation of mixing an in-organic gold source with a peptide solution.

8. The method of claim 7, wherein said peptide has an N-terminal and/or C-terminal having an amino acid of either Arg, Asn, Asp, Cys, Gln, Glu, His, Trp, or Tyr.

9. The method of claim 7, wherein said peptide contains nuclear localization signal sequence.

10. The method of claim 7, wherein said peptide contains a primary sequence targeting to a tyrosine kinase or cytoplasm.

11. The method of claim 7, wherein said peptide contains a mitochondria targeting primary sequence.

12. The method of claim 7, wherein said concentration of said peptide and Au(0) gold metal nano-cluster complex molecules contains less than 1000 μM gold.

13. The method of claim 1, wherein said concentration of said peptide and Au(0) gold metal nano-cluster complex molecules contains less than 100 μM gold.

14. A method of inducing cell death of specific cancer cell type, comprising the steps of:
    synthesizing a peptide having a primary sequence targeting to said cancer cell type;
    generating peptide and Au(0) gold metal nanocluster complexes with said peptide through a preparation of mixing an in-organic gold source with a solution of said peptide; and
    exposing said cancer cells to a concentration of said peptide and Au(0) gold metal nano-cluster complex molecules that inhibit TrxR enzyme activities of said cancer cells.

15. The method of claim 14, wherein said peptide has an N-terminal and/or C-terminal having an amino acid of either Arg, Asn, Asp, Cys, Gln, Glu, His, Trp, or Tyr.

16. The method of claim 15, wherein said peptide and Au(0) gold metal nano-cluster complex is generated by a one step method of mixing the peptide with a gold salt solution.

17. The method of claim 1, wherein said concentration of said peptide and Au(0) gold metal nano-cluster complex molecules contains less than 1000 μM gold.

* * * * *